US00PP08354P

United States Patent [19]

Tanno et al.

[11] Patent Number: Plant 8,354

[45] Date of Patent: Aug. 24, 1993

[54] APPLE TREE "AKITA GOLD"

[75] Inventors: Sadao Tanno, Hiraka; Jin Tanba, Yokote; Hiroshi Sato, Oomagari; Matuyori Kagaya; Tatuo Taguchi, both of Akita; Tanetugu Niizuma, Yokote, all of Japan

[73] Assignee: Akita Prefecture, Akita, Japan

[21] Appl. No.: 797,760

[22] Filed: Nov. 25, 1991

[51] Int. Cl.[5] ..... A01H 5/00

[52] U.S. Cl. ..... Plt./35.1

[58] Field of Search ..... Plt. 35.1

*Primary Examiner*—James R. Feyrer

*Attorney, Agent, or Firm*—Armstrong, Westerman, Hattori, McLeland & Naughton

[57] ABSTRACT

Disclosed is an apple tree having a moderate habit, a good spur-bearing habit and producing a medium size fruit maturing in the middle season similar to "Golden Delicious". The fruit has a conical to long conical shape, a dull appearance of dots, and a yellow skin. The flesh of the fruit is yellow, very juicy and crisp, has a moderate sweetness and acidity, and an aromatic flavor. Particularly, the storability of the fruit is significantly higher than that of "Golden Delicious", thereby providing the fruit with an excellent market value.

13 Drawing Sheets

BACKGROUND OF THE VARIETY

The present invention relates to a new and distinct variety of apple tree having a moderate habit and, especially, excellent storability, and less subject to wounding of the fruit surface and fruit drop during the maturation period.

In Japan, the "Golden Delicious" has been widely cultured instead of Jonathan and Rolls Janet because of its precocious bearing habit, good harvest and excellent taste. However, "Fuji" and "Ōrin", with a high storability, have become available in recent years, so that the availability of Golden Delicious has decreased abruptly as "Golden Delicious" has an essentially poor storability.

Our breeding has been aimed at obtaining a new variety of yellow-skin apple having a high market value, a higher storability, compared with "Golden Delicious", and subject to little wounding of the fruit surface and little fruit drop during the maturation period. Cultivation and breeding at an experimental station have been ongoing since 1966.

Accordingly, one purpose of our breeding program is to provide improved varieties of apple trees that can replace "Golden Delicious".

ORIGIN AND ASEXUAL REPRODUCTION OF THE VARIETY

One new variety of apple tree was a cross-seedling that resulted from a crossing between "Golden Delicious" (♀) (the seed parent) having excellent fruit quality with a yellow skin, and "Fuji" (♂) (the pollen parent) having excellent fruit quality and storability, at the Akita Fruit-Tree Experiment Station, 65 Aza-Kaido-shita, Daigo, Hiraka-Machi, Hiraka-gun, Akita-ken, Japan.

Specifically, the crossing was carried out at the station in 1974, seeds were obtained, and the same were sown in a field at the station the following year, 1975, thereby raising 80 seedlings. In 1977, said seedlings, as a number of seedling line 15-9-16, were top-grafted on "Redgold" (rootstock was *Malus prunifolia* Borkh. var. ringo Asami), and an evaluation of the same was started. The trees bore fruit in 1981, and the fruit obtained had excellent storability. The tree was used for primary selection for the purpose of providing evaluation characteristics thereof and the tree was top-grafted again on the rootstock, and the top-grafted tree started bearing fruit in 1986. The top-grafted tree was then examined for various characteristics, such as storability, cultivation characteristics of the tree and the like, and it was found that the tree was distinguishable from "Golden Delicious" and "Ōrin", which are the most closely related to the present variety. Accordingly, we named the said variety "Akita Gold" which is the subject of the present invention. The genus and species of the tree is "*Malus pumila* Miller var. domestica Schneider".

Of the varieties, "Golden Delicious" and "Ōrin", the former is a maternal variety, while the latter is a variety generated from a crossing between "Golden Delicious" and "Indo", and was allocated an increased area for growing in Japan. It is an attractive variety in that it has a flower similar to "Indo".

We asexually reproduced this new and distinct variety of apple tree "Akita Gold", by grafting, at the Fruit tree Experiment Station, Akita Prefecture, and confirmed the homogeneity and stability of "Akita Gold" according to this invention.

An application for this new variety of apple tree "Akita Gold" under the Seeds and Seedling Law of Japan was filed on Jul. 11, 1990, under the filing number 3997.

SUMMARY OF THE VARIETY

This new variety of apple tree has a moderate spreading habit, and is therefore similar to that of "Golden Delicious", but it is different from "Ōrin" in that the latter is upright. Although, fruit of the tree can be harvested in mid-October, just as with "Golden Delicious", it is distinguishable from "Ōrin", which is harvested in late October in the north-west regions of Japan. With respect to shape of the leaf, the new variety has a dull serrate leaf. "Golden Delicious" and "Ōrin" both have a sharp serrate leaf. The color of the petal of the tree is a light-pink (J.H.S.C. 5RP 9501, corresponding to "pale purplish pink" in ISCC - NBS chart), while the other said varieties are colored with a deep-pink (J.H.S.C. 5RP 9503 corresponding to "light purplish pink" in ISCC - NBS chart) in the central area of the reverse side thereof. (Color values presented are from the Japanese Horticultural Society Color Chart (J.H.S.C.) with reference to the corresponding color description in the ISCC - NBS color chart.)

The shape of the fruit of the tree is concial to long conical, whereas that of the "Golden Delicious" is oblong, and that of the "Ōrin" is ellipsoid and so that these varieties are distinguishable from each other.

The present fruit has a crown, whereas, both of the reference fruits do not have a crown. The present fruit has a smooth surface, but both of the references have rough surfaces blemishes, cracks and are russet. In the flesh of the present fruit is a water core, but the references do not contain a water core in the flesh. The fruit of the present invention is capable of being stored for five months in a refrigerator, but that of "Ōrin" and "Golden Delicious" can only be stored for three and two months, respectively, under similar circumstances. Further, the flesh of the present tree has a stronger Quince aroma than "Ōrin", and "Golden Delicious" substantially does not have the aroma.

DESCRIPTION OF THE VARIETY

Figure 1:
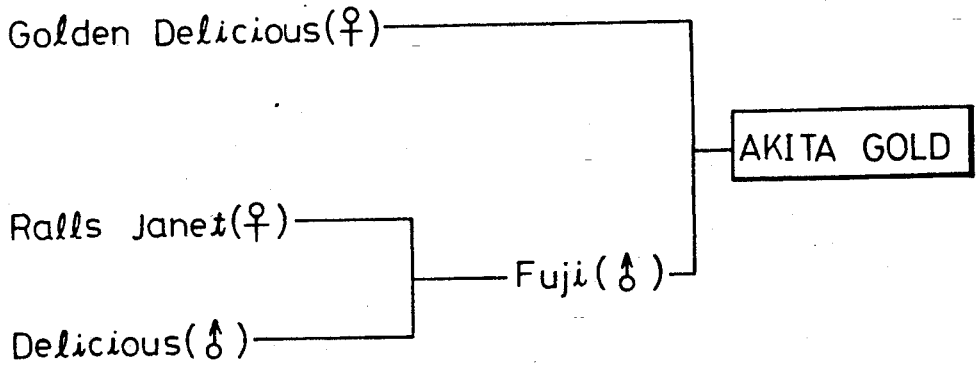
FIG. 1 gives the pedigree of the new and distinct variety of the apple tree "Akita Gold"
Figure 2:
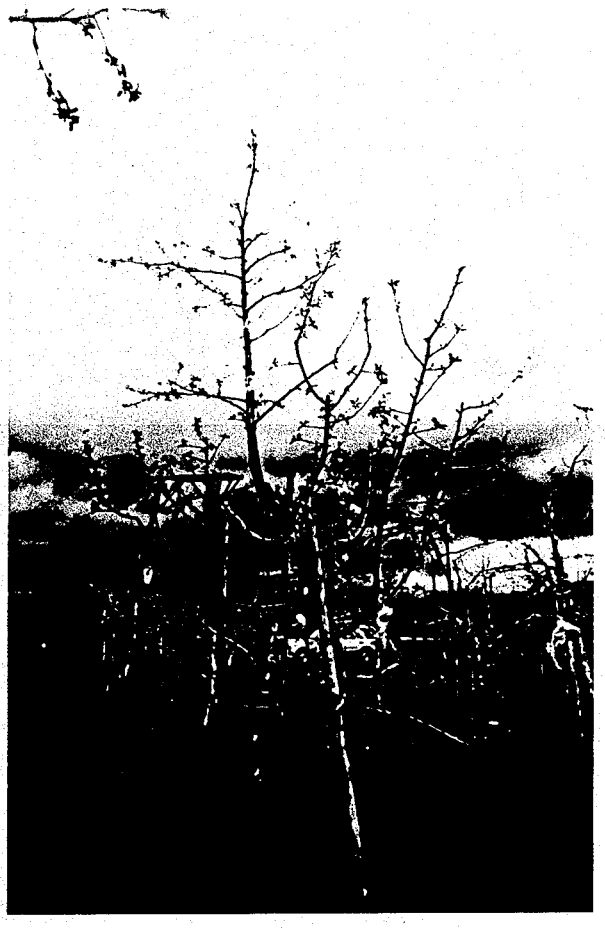
FIG. 2 is a photograph of a shape of the new variety of apple tree.
Figure 3:
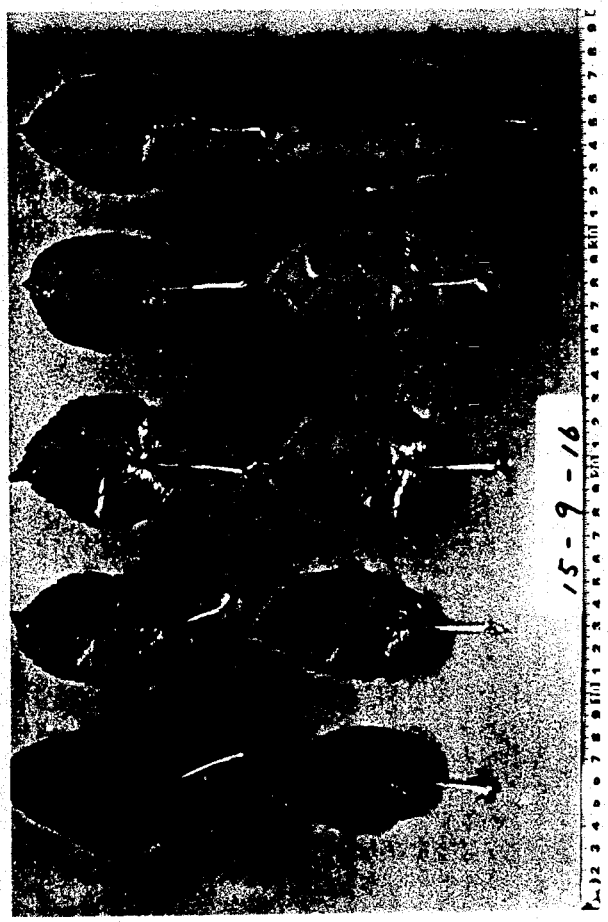
FIG. 3 is a photograph of adult leaves (upper side) of the new variety of apple tree.
Figure 4:
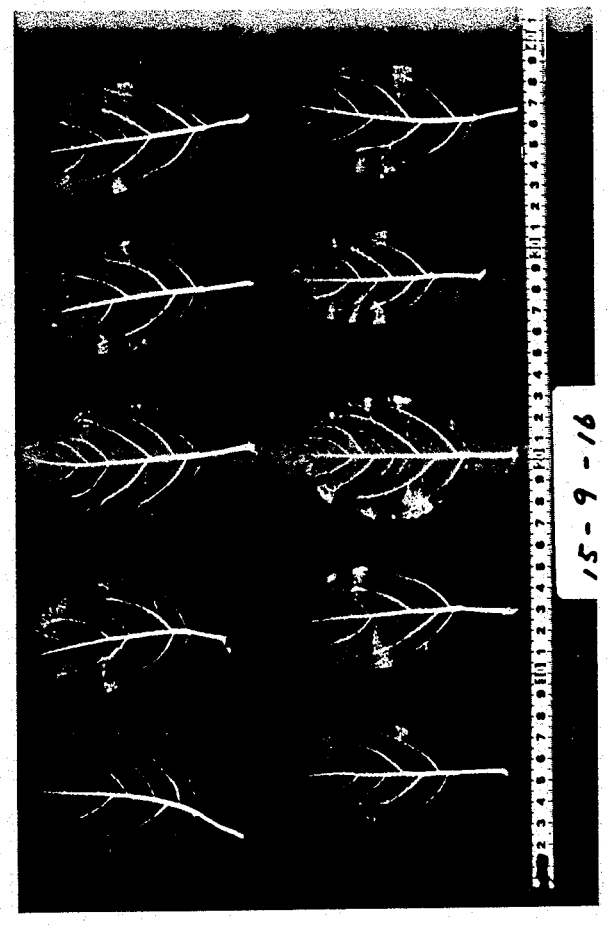
FIG. 4 is a photograph of adult leaves (reverse side) of the new variety of apple tree.
Figure 5:
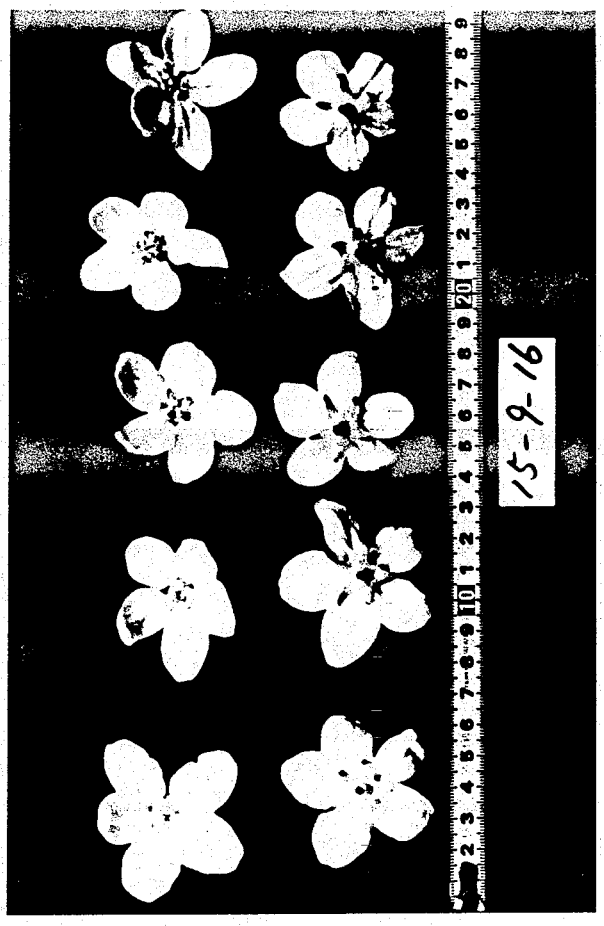
FIG. 5 is a photograph of the flowers of the new variety of apple tree.
Figure 6:
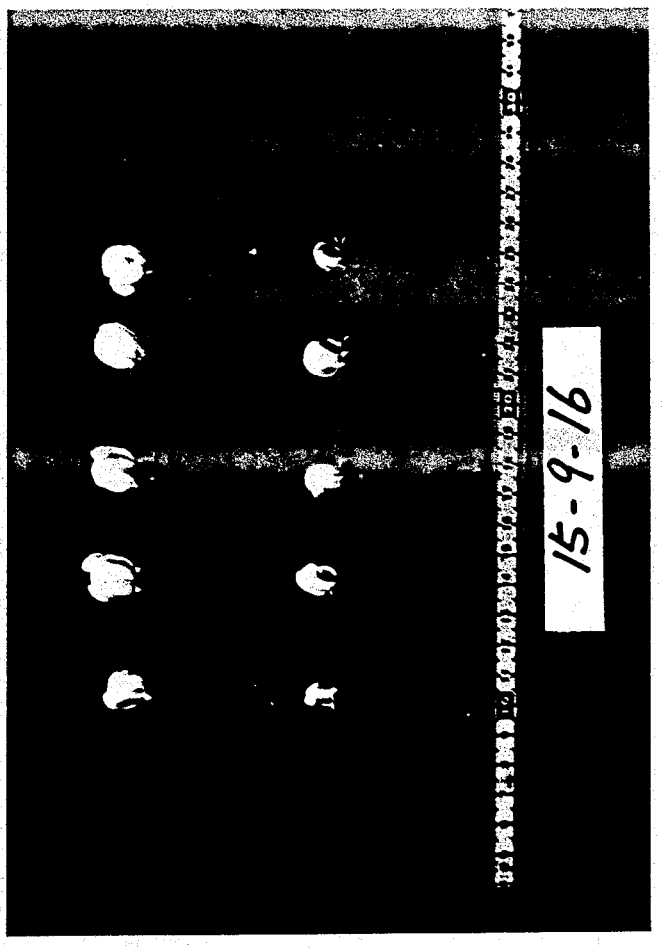
FIG. 6 is a photograph of the flower buds of the new variety of apple tree.
Figure 7:
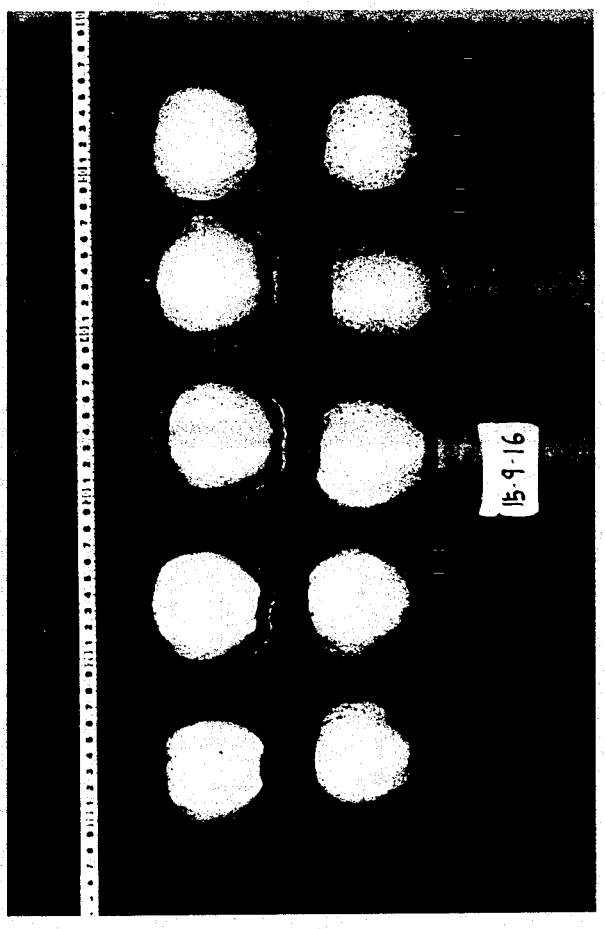
FIG. 7 is a photograph of side views of the fruit of the new variety of apple tree.
Figure 8:
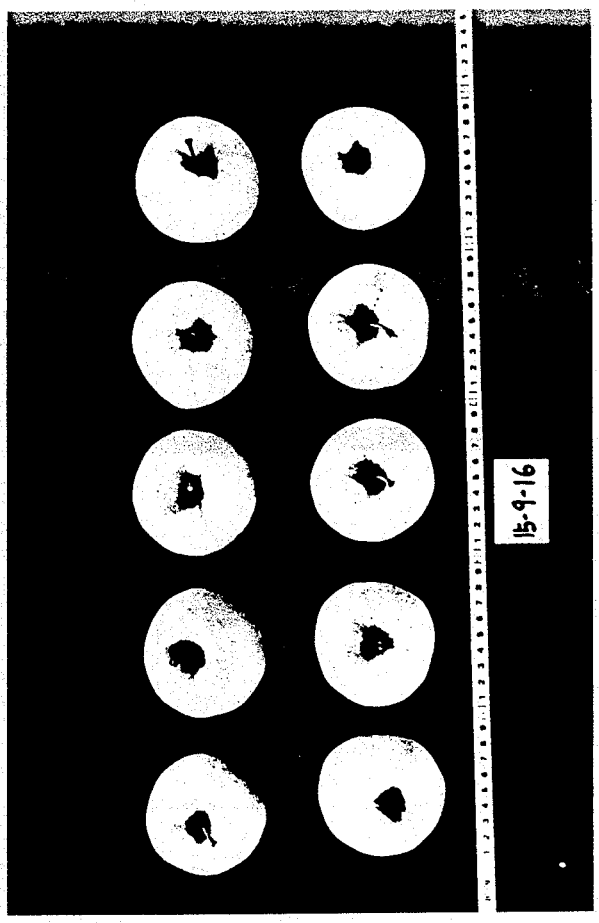
FIG. 8 is a photograph of cavities of fruit of the new variety of apple tree.
Figure 9:
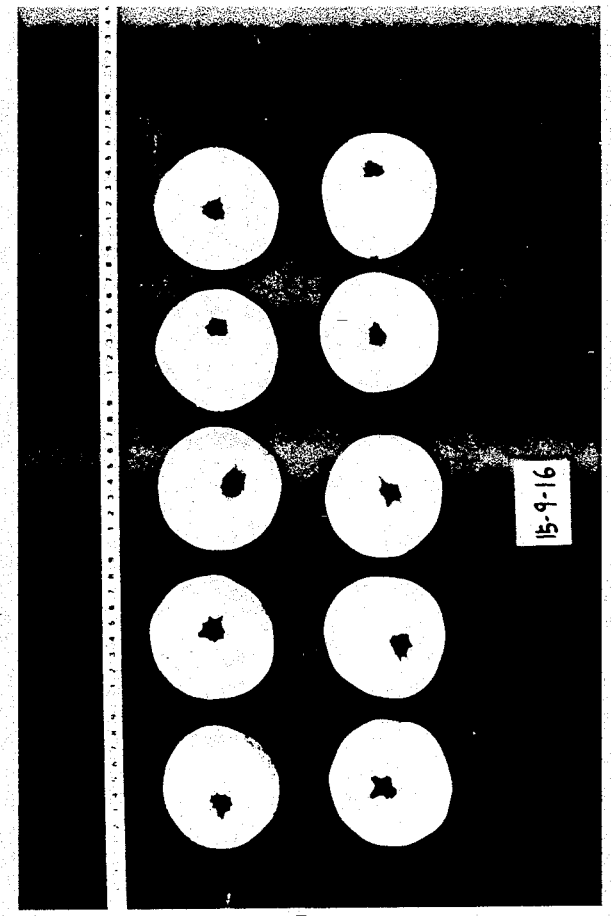
FIG. 9 is a photograph of basins of fruit of the new variety of apple tree.
Figure 10:
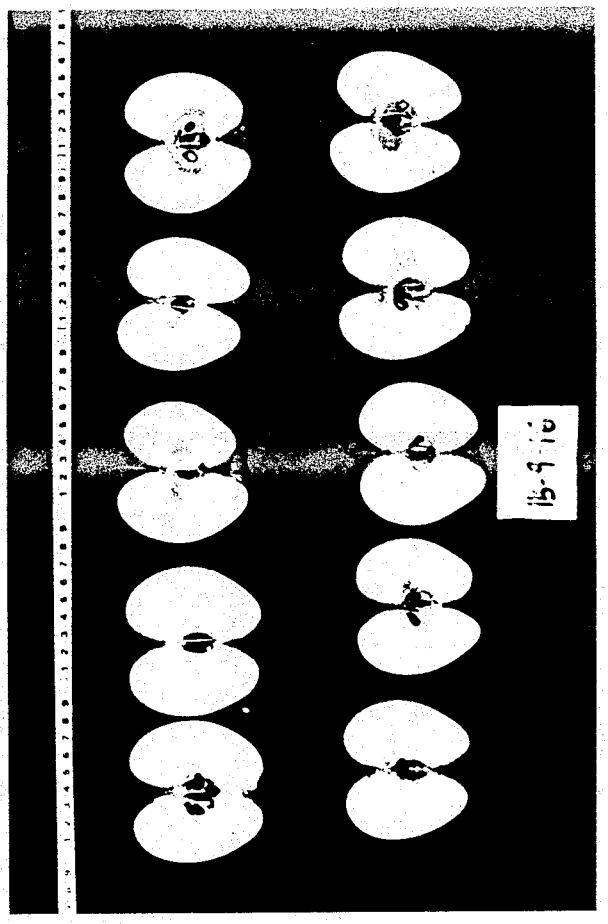
FIG. 10 is a photograph of longitudinal-sectional views of fruit of the new variety of apple tree.
Figure 11:
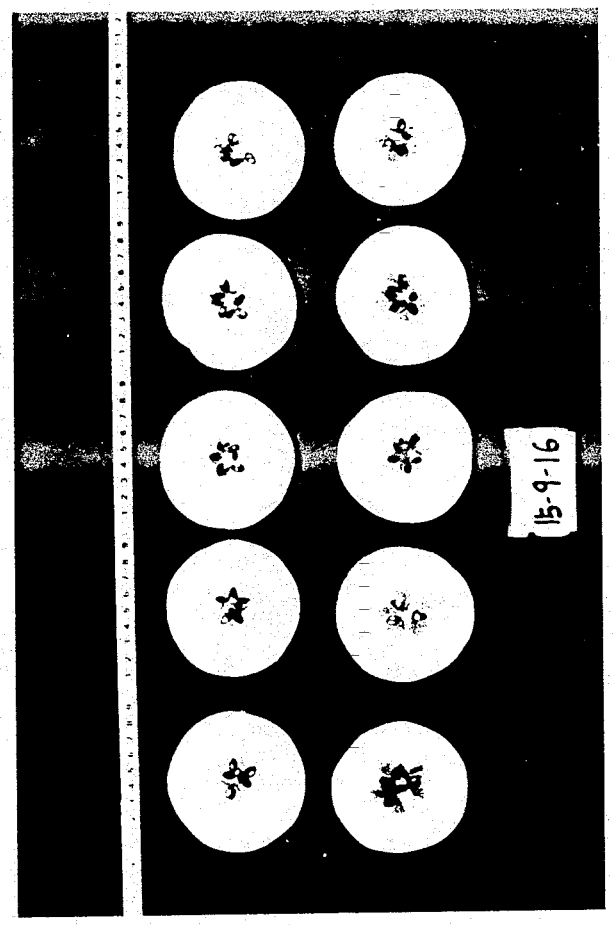
FIG. 11 is a photograph of cross-sectional views of fruit of the new variety of apple tree.
Figures 12, 16:
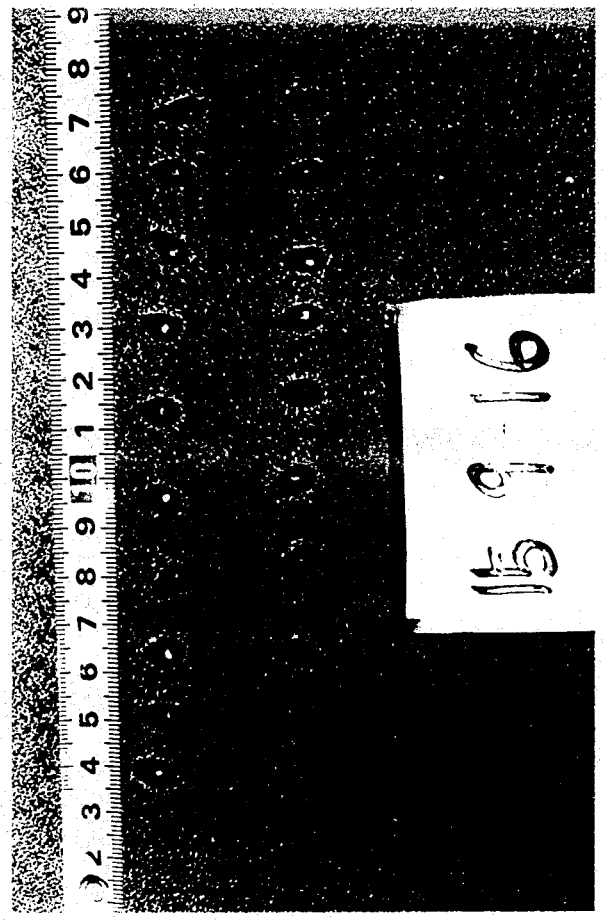
FIG. 12 is a photograph of seeds of the new variety of apple tree.
Figure 13:
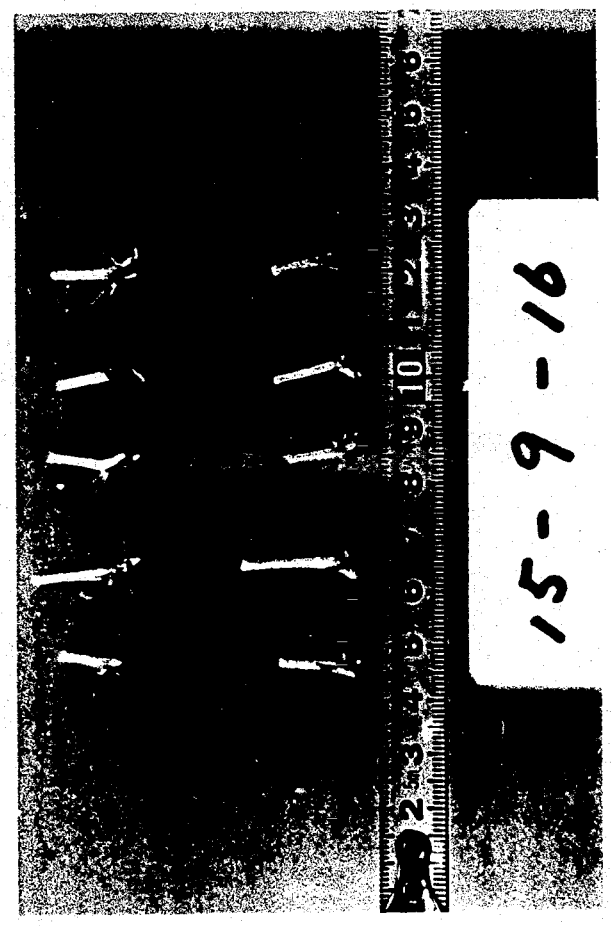
FIG. 13 is a photograph of stipules of the new variety of apple tree.

The characteristics of the new and distinct variety of apple tree "Akita Gold" are as follows:

Tree:

*Shape.*—Medium, same as "Golden Delicious".

*Habit.*—Increasing substantially, the same as "Golden Delicious", the tree has the same chilling requirements and hardness as the other apple trees cultured in Japan.

*Spur.*—Abundantly bearing, the percentage of the number of spur to the total of terminal buds is 67.0.

*Predominance of axillary flower bud.*—Medium, same as "Fuji".

*Time of bud break.*—Medium, later than "Ōrin", but earlier than "Fuji".

*Production.*—As productive as "Golden Delicious". Little biannual production. Abundant fruiting every year with appropriate fruit thinning.

*Fertility of pollen.*—Good, fruit set percentage per crossing together with other main commercial varieties is high.

Branches:

*Thickness (one-year-old shoot).*—Medium, same as "Fuji".

*Size of lenticel (one-year-old shoot).*—Small, same as "Fuji".

*Length of internode.*—Medium, 3.18 cm.

*Number of lenticel.*—Abundant, the number is 184, lenticels of "Golden Delicious" and "Ōrin" are 158 and 166, respectively, per 10 cm of same.

*Color of lenticel.*—Reddish-brown (J.H.S.C.6YR 1615, corresponding to "pale yellowish pink" in the ISCC - NBS chart), which is lighter than that of "Fuji".

Leaves:

*Shape.*—Oval, similar to "Fuji".

*Serrations.*—Dull serrate.

*Size.*—Medium, same as "Fuji". The leaf has a size of about 9.3 cm in length, which is shorter than "Ōrin", and about 5.2 cm in width.

*Color.*—Green (J.H.S.C.3G 4309, corresponding to "strong green" in the ISCC - NBS chart), a little bit lighter than "Ōrin".

*Petiole.*—Short, the petiole has a length of about 2.54 cm which is the same as "Fuji", and is shorter than that of A "Ōrin"; the thickness of petiole is thin, 0.20 cm, which is the same as "Fuji".

*Stipule.*—Small. The stipule is a little bit smaller than that of "Ōrin", and has a size of about 0.58 cm in length and about 0.12 cm in width. The stipule has a sickle shape.

Flowers:

*Flower number in a flower cluster.*—Medium, 5 to 6 per cluster.

*Size (opened flower).*—Medium, 5.17 cm in diameter and larger than "Fuji".

*Color (unopened flower).*—Light pink (J.H.S.C.5RP 9503, corresponding to "light purplish pink" in the ISCC - NBS chart), lighter than "Ōrin" and "Golden Delicious".

*Shape of petals.*—Oval, length/width=1.56, a little longer than "Fuji". The petals are about 2.32 cm in length and about 1.49 cm in width.

*Color of petals.*—White (J.H.S.C.2RP 9201, corresponding to "purplish white" in the ISCC - NBS chart) (upper side) and pink (J.H.S.C.5RP 9502, corresponding to "pale purplish pink" in the ISCC - NBS chart) (reverse side) same as "Golden Delicious".

*Number of petals.*—Medium, 5 petals.

*Number of stamens.*—Medium, 20–21 stamens, same as the other varieties.

*Color of anthers.*—Light yellow (J.H.S.C.5Y 2504, corresponding to "light yellow" in the ISCC - NBS chart).

*Number of pollen.*—Medium. Percentage of fertility is 97.8 percent.

*Flowering time.*—Medium in the season; slightly later than "Ōrin" and faster than "Fuji".

Fruit:

*Size.*—Medium (about 278 g).

*Shape.*—Conical to long conical.
*Crowning at eye end.*—Medium.
*Aperture of eye.*—Shallow.
*Depth of basin.*—Medium (1.17 cm), close to "Fuji".
*Breadth of basin.*—Medium (3.31 cm), narrower than "Fuji".
*Depth of stalk cavity.*—Medium (1.70 cm).
*Breadth of stalk cavity.*—Broad (3.81 cm), almost the same breadth as "Fuji".
*Color of skin.*—Yellow (J.H.S.C.7Y 2703, corresponding to "light greenish yellow" in the ISCC - NBS chart), same as "Golden Delicious".
*Type of cover color of skin.*—Yellow (J.H.S.C.5Y 2505, corresponding to "brilliant yellow" in the ISCC - NBS chart), lighter than "Golden Delicious".
*Amount of russet.*—Absent.
*Shape of lenticel.*—Round.
*Size of dots.*—Medium.
*Number of dots.*—Few, fewer than "Golden Delicious".
*Silvery mottle of skin.*—Absent.
*Shininess of skin.*—Moderate.
*Greasiness of skin.*—Moderate.
*Bloom of skin.*—Absent.
*Cracking tendency of skin.*—Absent.
*Surface texture of skin.*—Smooth.
*Length of stalk.*—Long (3.38 cm).
*Thickness of stalk.*—Medium (0.20 cm), slender than "Fuji".
*Distinct swelling at end of stalk.*—Absent.
*Size of core.*—Medium, length cut core/length cut fruit=39.5 percent.
*Shape of core.*—Refer to photographs 10 and 11.
*Number of core cells.*—Medium.
*Color of the flesh.*—Yellow (J.H.S.C.5Y 2503, corresponding to "pale yellow" in the ISCC - NBS chart), same as "Golden Delicious" and "Fuji".
*Browning of the flesh.*—Medium, ssame as "Ōrin" and "Fuji".
*Firmness of the flesh.*—Firm.
*Texture of the flesh.*—Fine.
*Water core (glassiness).*—Strong.
*Sweetness of the flesh.*—Medium, refractometer index is 13 to 15 percent.

*Acidity of the flesh.*—Medium, content of maleic acid is 0.45 to 0.55 percent, slightly stronger than "Fuji".
*Astringency of the flesh.*—Absent.
*Flavor of the flesh.*—Strong, same as "Starking Delicious".
*Juiciness of the flesh.*—Juicy.
*Maturity.*—Mid-October in area of Akita-ken, in Japan, medium maturing cultivar.

Seed:
*Number of fully developed seeds.*—Many (over 10). Shape of seeds: Ovovoid. Size of seeds: Medium.

Physiological and ecological characteristics:
*Predominancy of precocity.*—Medium, start bearing at 3 years old (using M. 26 rootstock).
*Self-fruitfulness.*—Medium.
*Early drop of fruit.*—None or slight.
*Preharvest drop of fruit.*—None or slight.
*On-tree storage.*—Excellent. No mealiness and deterioration in fruit quality. No fruit drop after harvesting season.
*Physiological disorder of the fruit.*—Medium.
*Keeping quality of fruits I (ordinary storage).*—Long, at room temperature for 20 to 30 days.
*Keeping quality of fruits II (cold storage).*—Long, in refrigerator after 5 months the fruits maintain 14 pounds.
*Occurrence of core rot.*—None or minimal.
*Resistance to alternaria blotch.*—Moderate.
*Resistance to powdery mildew.*—Moderate.
*Resistance to aphid.*—Moderate.
*Resistance to other diseases.*—Moderate.

We claim:

1. A new and distinct variety of apple tree, substantially as illustrated and described herein, characterized over known apple trees by (A) having a moderate habit, and (B) producing a medium size fruit having a conical to long conical shape, (a) maturing in the middle season, and (b) having (1) an excellent storability compared with "Golden Delicious", which is the seed parent, (2) a dull appearance caused by few dots of medium size against a yellow colored surface, which overlays a yellow ground color skin, and (3) a yellow flesh that is juicy and crisp, has a moderate sweetness and acidity, an aromatic flavor, provides a good sweet-acid balance and has excellent consumption quality.

* * * * *

Pedigree